United States Patent [19]

Gebel

[11] Patent Number: 4,752,349
[45] Date of Patent: Jun. 21, 1988

[54] DISPOSABLE ABSORBENT PRODUCT HAVING RESILIENT SCALLOPED EDGE, AND METHOD OF MAKING THE PRODUCT

[75] Inventor: James M. Gebel, Cincinnati, Ohio

[73] Assignee: The Procter & Gamble Company, Cincinnati, Ohio

[21] Appl. No.: 834,688

[22] Filed: Feb. 28, 1986

[51] Int. Cl.$^4$ .................. B32B 31/18; B32B 31/26
[52] U.S. Cl. ..................... 156/267; 156/251; 156/269; 156/290; 156/308.4; 604/380; 604/385 R
[58] Field of Search ............... 604/398, 365, 366, 367, 604/369, 370, 378, 380, 385 R; 156/308.4, 290, 269, 250, 251, 267, 222

[56] References Cited

U.S. PATENT DOCUMENTS

| | | | |
|---|---|---|---|
| D. 247,372 | 2/1978 | Whitehead | 604/358 |
| 3,315,676 | 4/1967 | Cooper | 604/370 |
| 3,369,547 | 2/1968 | Sack et al. | 156/251 |
| 3,442,268 | 5/1969 | Bird | 604/366 |
| 3,477,433 | 11/1969 | Dillon | 604/370 |
| 4,300,562 | 11/1981 | Pieniak . | |
| 4,321,924 | 3/1982 | Ahr . | |
| 4,323,069 | 4/1982 | Ahr et al. . | |
| 4,332,253 | 6/1982 | Schoots | 604/365 |
| 4,333,782 | 6/1982 | Pieniak . | |
| 4,397,645 | 8/1983 | Buell | 604/380 |
| 4,407,284 | 10/1983 | Pieniak | 604/385 |
| 4,463,045 | 7/1984 | Ahr et al. . | |
| 4,650,481 | 3/1987 | O'Connor et al. | 604/366 |

Primary Examiner—C. Fred Rosenbaum
Assistant Examiner—Denise Whelton
Attorney, Agent, or Firm—J. M. Pollaro; F. H. Braun; R. C. Witte

[57] ABSTRACT

A disposable absorbent product such as a panty liner (or pantiliner) or sanitary napkin or product for incontinents having a resilient, scalloped perimetrical edge, and a method of making the product. In a preferred laminated embodiment, a resilient absorbent core lamina is disposed between and coextensive—at least in their edge areas—with a liquid permeable topsheet and a liquid barrier backsheet. The elements are bonded together by a multiplicity of perimetrically spaced, compacted bonded areas which impart a scalloped character to the edge of the product, and wherein each scallop is filled with an edge portion of the resilient absorbent core lamina. Each bonded area is preferably elongate, and orthogonally disposed with respect to the edge of the product; and, preferably, each bonded area comprises a plurality of concatenated discrete bonds for improved flexibility.

4 Claims, 2 Drawing Sheets

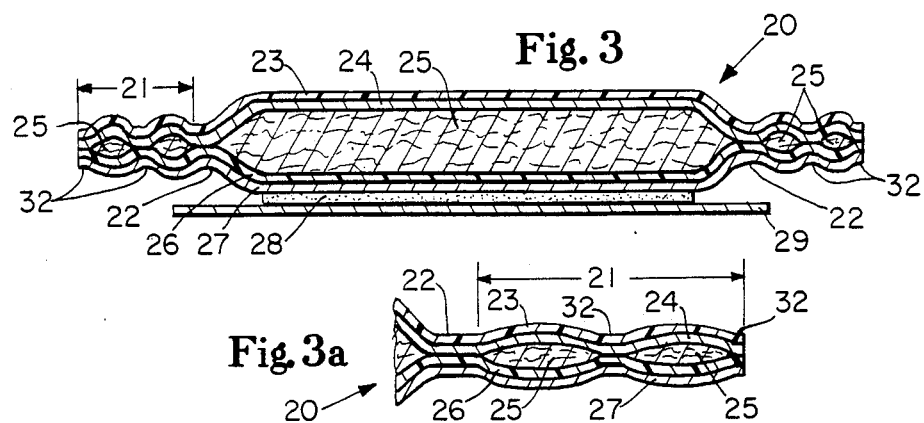
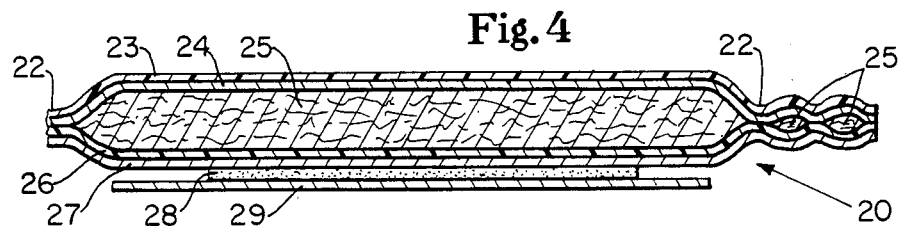
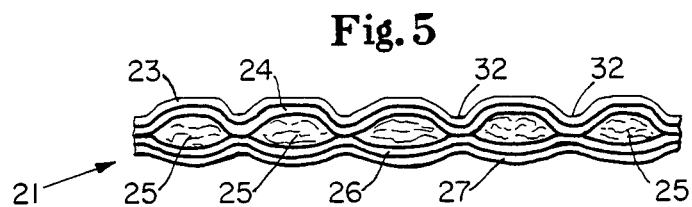
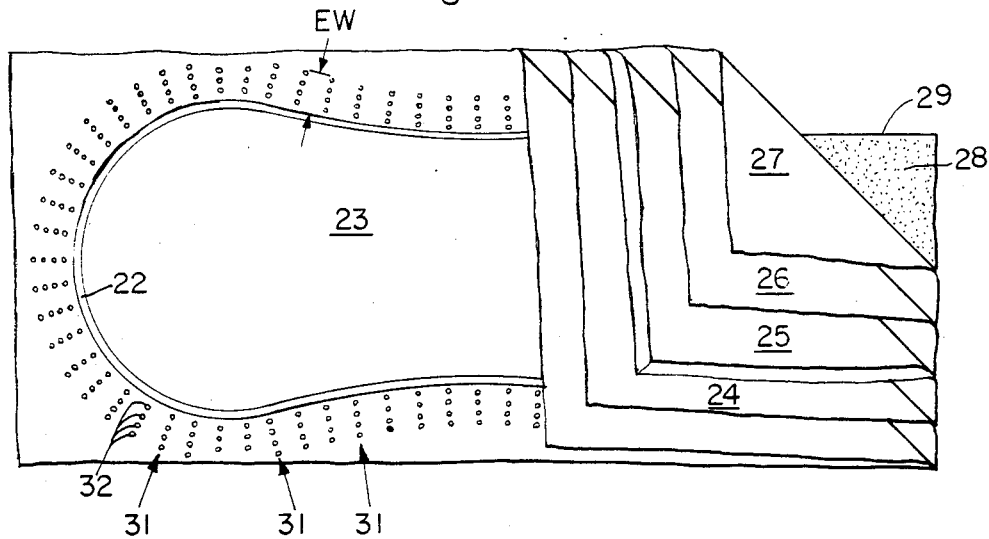

DISPOSABLE ABSORBENT PRODUCT HAVING RESILIENT SCALLOPED EDGE, AND METHOD OF MAKING THE PRODUCT

DESCRIPTION

1. Technical Field

This invention pertains to disposable absorbent products and methods of making such products. More specifically, it pertains to absorbent products such a panty liners, sanitary napkins, and products for incontinents comprising plural layers which are joined together along their edge regions in such a manner that their perimetrical edges are scalloped, resilient, and flexible.

2. Background Art

Disposable absorbent products having elastically gathered edge portions are disclosed in U.S. Pat. Nos. 4,300,562; 4,333,782; 4,397,645; and 4,407,284. Edge portions wherein scalloped topsheet and scalloped backsheet edges are disposed on opposite sides of an ungathered elastic lamina are shown in FIGS. 7, 9 and 11 of U.S. Pat. No. 4,397,645 which issued Aug. 9, 1983. However, as compared to the present invention, the scalloped zones on both sides of the elastic lamina are hollow: i.e., not filled with resilient edge portions of a resilient layer of the product which is coextensive with the topsheet and backsheet of the product.

Additionally, U.S. Pat. No. 4,321,924 which issued Mar. 30, 1982 to Nicholas A. Ahr is representative of layered disposable products wherein two or more layers have their edge regions bonded together to form ungathered, non-elasticized perimetrical borders and which, additionally, are not resilient.

DISCLOSURE OF THE INVENTION

In one aspect of the present invention, a disposable absorbent product is provided which comprises plural coextensive layers which are coextensive in at least their edge areas. The layers include a topsheet, a backsheet and a resilient absorbent core which may be a high loft fibrous web. Coextensive edge areas of the layers are bonded together in such a manner and pattern that the edge of the product is scalloped, and each scallop is a resilient pillow which comprises an edge portion of the resilient core that is disposed between edge portions of the topsheet and the backsheet. In a preferred embodiment, the layers are bonded or otherwise joined together in a multiplicity of perimetrically spaced bonded zones; and the spaced bonded zones are elongate and oriented orthogonally with respect to the perimetrical edge of the product. Additionally, each elongate bonded zone preferably comprises a linear array of concatentated discrete bonds for improved flexibility. In another aspect of the invention, a method of making such a disposable product is provided which includes the steps of providing juxtaposed webs of the layer materials which webs are larger in area than the product to be made; joining or bonding the web layers together with a pattern of discrete bonded zones which span a desired line of parting along which the product is to be served to separate the product from the waste edge portions of the webs; and severing the layers along the line of parting. By spanning the desired line of parting, the actual line of parting may be somewhat out of registration yet still precipitate the desired resilient, scalloped edge construction.

BRIEF DESCRIPTIONS OF THE DRAWINGS

While the specification concludes with claims which particularly point out and distinctly claim the subject matter regarding as forming the present invention, it is believed that the invention will be better understood from the following description taken in conjunction with the accompanying drawings in which thicknesses of this laminae have been exaggerated to clearly show their presence, and in which:

FIG. 3 is a sectional view taken along line 3—3 of FIG. 2.

FIG. 3a is an enlarged scale, fragmentary sectional view taken along section line 3—3 of FIG. 2.

FIG. 4 is a sectional view taken along line 4—4 of FIG. 2.

FIG. 5 is an enlarged scale, edge view of a fragmentary portion of the FIG. 1 embodiment of the invention.

FIG. 6 is a plan view of a partially fabricated sample of the embodiment of the invention shown in FIG. 1.

DETAILED DESCRIPTION OF THE INVENTION

Figure 1:
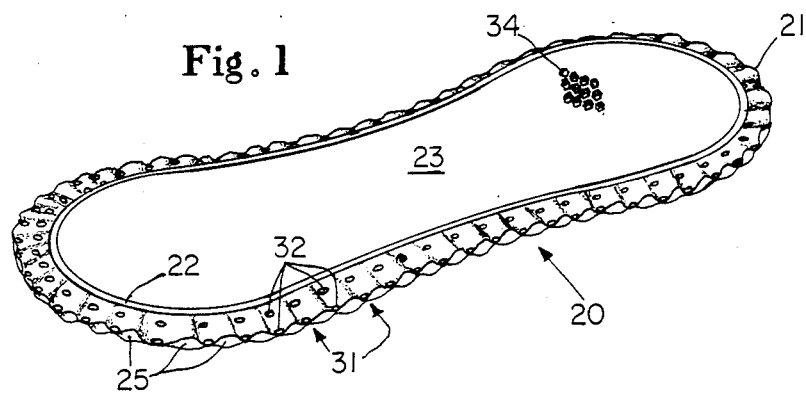
FIG. 1 is a perspective view of an exemplary panty liner embodiment of the invention.

A disposable absorbent article—panty liner 20 which is an exemplary embodiment of the present invention—is shown in perspective in FIG. 1 to have a scalloped perimetrical edge 21 that extends outwardly from an endless perimetrical seal 22. As also shown in FIG. 1, panty liner 20 comprises a topsheet 23; and a resilient core 25, edge portions of which fill the scallops of perimetrical edge 21. While the invention is discussed through describing a panty liner it is to be understood that the invention pertains generally to absorbent articles which includes, but is not limited to panty liners, sanitary napkins, and absorbent products for incontinents, and the like.

Briefly, the present invention provides a layered absorbent article and method of making the article so that the article has a resilient, scalloped edge about its entire perimeter. Such a resilient edge provides improved ongoing perimetrical conformation to the user's anatomy while in use, and provides a high degree of user comfort. In a preferred embodiment comprising plural layers of web material, perimetrically spaced radial rows of discrete bonds secure coextensive layers of the perimeter of the article together. The discrete bonds of each row are said to be concatentated by virtue of being closely spaced, and linked together by intervening portions of the web. The scallops are precipitated by the pattern of bonding and because an inner layer 25 of the article is sufficiently resilient to puff up between adjacent rows of compacted bonds; and each scallop is filled with an edge portion of the resilient layer. The method includes the step of bonding the layers together with a bonding pattern comprising a pattern of radial rows of spot bonds which rows are longer than the desired width of the article's edge. Then, the article is cut from the parent webs along a line of parting. By virtue of the rows of bonds being longer (i.e., in their radial dimension) than the desired width of the article's edge, registration between the bonding apparatus and the cutting apparatus is not critical.

Figure 2:
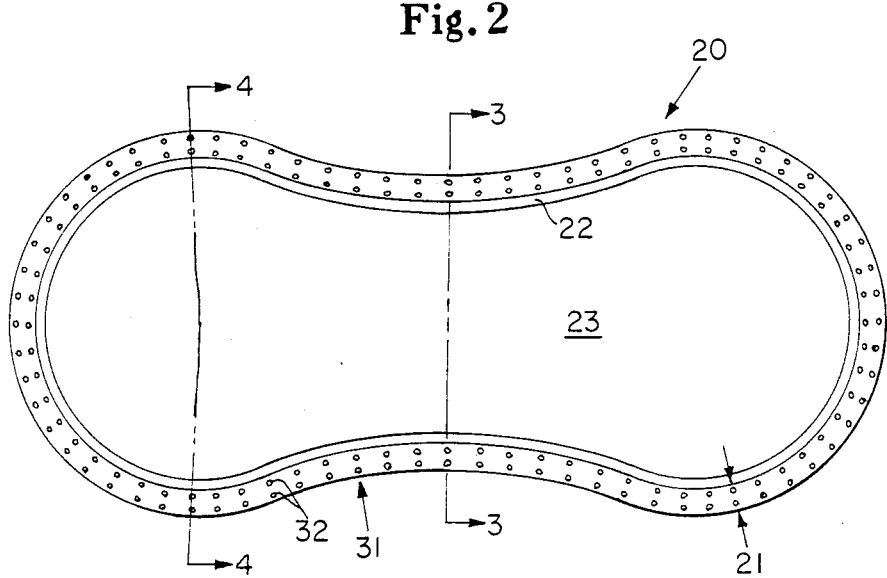
FIG. 2 is a plan view of the panty liner of FIG. 1.

Referring now to FIGS. 2 (plan view), 3 (sectional view along line 3—3 of FIG. 2), 3a (enlarged scale, fragmentary sectional view along line 3—3 of FIGS. 2), and 4 (sectional view along line 4—4 of FIG. 2), panty liner 20 further preferably comprises a wicking layer 23, a barrier layer 26, a back cover 27, a layer of pressure sensitive panty fastening adhesive 28, and, until panty liner 20 is prepared for use, a removable back protector 29. Thus, referring to FIGS. 3 and 4, the entire assembly of panty liner 20 consists of, from top (wearer side) to bottom (outside), topsheet 23, wicking layer 24, resilient core 25, barrier layer 26, back cover 27, panty fastening adhesive 28, and the removable back protector 29. It is, however, not intended to thereby limit the present invention to embodiments comprising all such elements, or to thereby preclude additional elements.

Referring back to FIG. 1, perimetrical edge 21 is the edge portion of panty liner 20 that is disposed outboard from perimetrical seal 22; and which is characterized by a multiplicity of perimetrically spaced, radially outwardly extending, elongate zones of bonding. Preferably, each of the elongate zones of bonding, generally indicated by pointers 31, comprises a plurality of spaced, discrete bonds 32. In FIG. 1, the discrete bonds 32 of each elongate zone of bonding are linearly arrayed to form a radially oriented row of discrete bonds. The closely spaced discrete bond areas per se are interconnected by intervening portions of the layers, and are therefore said to be concatentated: i.e., hinged or connected together. Whereas the bonded areas per se may be relatively hard and stiff, the lines of bonds 31 are flexible because of the unbonded interconnections.

FIG. 4 is an enlarged scale, fragmentary view of perimetrical edge 21 as it would appear to one looking directly at edge 21 along a line of sight in the plane of the edge and perpendicular thereto. This shows the pillow shape portions of resilient core 25 disposed between adjacent bonds 32 (on each side), and the other laminae of the construction (on the top and bottom).

Topsheet 23, FIG. 1, is fluid pervious by virtue, for example, of being perforated by a multiplicity of fine holes 34 which precipitate a net-like appearance. While it may be of nonwoven or woven or other materials, the Macroscopically Expanded Web disclosed in U.S. Pat. No. 4,463,045 is net-like and has been found to be a very desirable and useful topsheet material. An exemplary such expanded web may be made, for example, of polyethylene.

Wicking layer 24, FIG. 3, is a layer of tissue paper: for example, high bulk tissue paper having a basis weight of about 15 pounds per 3000 square feet (about 24.5 grams per square meter). However, satisfactory wicking may alternatively be achieved through the use of a fibrous coating on the back surface of topsheet 23 as disclosed in U.S. Pat. No. 4,323,069.

Resilient absorbent core 25, in FIG. 3, is preferably a high loft fibrous batt or web. For example, a batt of polyester fibers of from about 4 to about 15 denier which are bonded together by latex; and which batt has an uncompressed thickness of from about 3 mm to about 10 mm, and weight of about 3 ounces per square yard (about 102 grams per square meter) has been found to be very effective as the absorbent core member of a panty liner embodiment of the present invention. While, preferably, the resilient absorbent core comprises a mass or batt of fibers, it can comprise other materials, such as a synthetic foam material, such use is less preferred than the use of a fibrous batt.

The resilient absorbent core is preferably sufficiently resilient that, without the application of external forces, it will return to essentially its original size and shape after deforming forces are removed. Preferably, the resilient absorbent core possesses sufficient such resilience that it will recover at least about 80% of its original volume after it is compressed to about 20% of its original volume and the compressing forces are removed. Its resilience should be essentially unaffected by the presence of moisture such as the moisture in vaginal discharges; that is to say, the resilient absorbent core should be essentially moisture insensitive.

The resilient absorbent core should be of relatively low density so that it has sufficient void volume to contain practical quantities of vaginal discharges. Low density can also help to insure that the resilient absorbent core is readily deformable under the influence of the user's body thereby exhibiting comfort attributes. Preferably, the density of a fibrous resilient absorbent core is from about 0.01 to about 0.1 gram per cubic centimeter.

The surfaces of the interstices of the resilient absorbent core should be substantially hydrophilic. More generally, the resilient absorbent core should comprise a material which is wetted by the fluids in question. Vaginal discharges and other bodily fluids are primarily aqueous solutions and suspensions; surfaces which are wetted by these fluids can be broadly described as hydrophilic. As used in this specification, the term "hydrophilic" describes surfaces which are wetted by the fluid in question. Thus, the resilient absorbent core should be hydrophilic.

The surfaces of the interstices of the resilient absorbent core, and, in turn, the surfaces of the fibers, must be hydrophilic. Hydrophilicity can be achieved by selecting fibers which are inherently hydrophilic. The problem with achieving hydrophilicity by this method is that hydrophilic fibers, such as rayon, generally lose their resiliency in the presence of moisture. Preferably, then, synthetic fibers such as polyester are used and are treated with surfactant to render the surfaces hydrophilic while not materially diminishing the resilience of the resilient absorbent core.

Suitable surfactants include nonionic surfactants such as Brij 76 manufactured by ICI Americas, Inc. of Wilmington, Del. and the various materials sold under the Pegosperse tradmark by Glyco Chemicals, Inc. of Greenwich, Conn. Anionic surfactants can also be used. Surfactants are applied to the fibers at a level of from about 0.2 to about 1 gram per square meter of resilient absorbent core.

Synthetic fibers useful in the present invention include those made of cellulose acetate, polyvinyl chloride, polyvinylidene chloride, acrylic resins, polyvinyl acetates, non-soluble polyvinyl alcohols, polyethylenes, polypropylenes, polyamides, and, preferably, polyesters. Preferred polyester fibers have a denier of from about 4 to about 15 and a length of from about 2 to about 8 centimeters.

As indicated before, resiliency of the resilient absorbent core may frequently be enhanced if the fibers are bonded together at their points of contact. Thermal bonding may be used or, preferably, adhesives, such as latex adhesives, may be used to bond the synthetic fibers one to another.

Synthetic foams useful as the resilient absorbent core include polyester foam materials, polyurethane foams, styrene-butadiene foams, and cellulose sponge material. The synthetic foam should be soft and flexible, open celled, and of medium cell size. Its interior surfaces should be hydrophilic. Incorporation of surfactant during foam manufacture or addition of surfactant to the preformed foam are two suitable methods of insuring that the interior surfaces are hydrophilic. The foam should have a density of from about 0.1 to about 0.8 grams per cubic centimeter. The use of an overwrap with a synthetic foam resilient absorbent core may be optional.

Barrier layer 26, FIG. 3, is a fluid barrier layer or is impervious with respect to body fluids such as menses, urine, and the like. For example, a one mil film of polyethylene has been found to be very effective as a barrier layer 26.

Back cover 27, FIG. 3, is preferably a non-woven fibrous web of thermoplastic material such as, for example, meltblown polypropylene having a weight of about 0.55 ounces per square yard (about 18.8 grams per square meter), and a nominal caliper of about 0.25 mm to about 1.0 mm. Such a back cover has a soft feel and provides highly desirable user comfort, as well as pleasing esthetics.

Panty fastening adhesive 28, FIG. 3, is preferably a pressure sensitive adhesive that is provided to enable releasable attachment of panty liner 20 to the inwardly facing surface of a user's panties. Suitable such adhesives include Century A-305 IV manufactured by Century Adhesive Corporation; and Instant Lok 34-2823 manufactured by National Starch Company.

Removable back protector 29, FIG. 23, is provided to protect and preserve the functionality of adhesive 28 until a user wishes to attach the panty liner inside her panties. It is made of release material: i.e., material such as paper that is suitable coated to enable peeling it from adhesive 28. For example, release liners BL30MG-A SILOX E1-0, and BL30MG-A SILOX 4P/0 manufactured by Akrosil Corporation have been found to be suitable as back protectors 29.

Referring back to FIG. 2, the discrete bonds 32 are preferably effected by ultrasonic means which includes an anvil having a pattern of bond-precipitating protuberances having diameters of about 0.032 inches (about 0.8 mm), and which are spaced (for each row of bonds) about 0.062 inches (about 1.6 mm) center-to-center. At each such bond site, thermoplastic of the topsheet 23 and/or the barrier layer 26 penetrates the interstices of the portions of resilient layer 25 therebetween and effects bonding all of the layers together at the bond sites with intervening portions of resilient layer 25 highly compacted. It is, however, not intended to limit the present invention to ultrasonic bonds, or to bonds wherein material of any layer must flow through interstices of another layer.

One hourglass-shaped panty liner constructed in accordance with the invention and comprising the elements and materials delineated above is sized and configured as follows: length of about 15 cm; width across the widest zones (i.e. section line 4—4 of FIG. 2) of about 6.3 cm; width across the narrow central region (i.e., along section line 3—3 of FIG. 2) of about 5 cm; a perimetrical seal 22 having a width of about 2 to 2.5 mm; and a scalloped perimetrical edge 21 that extends outwardly about 3 to about 4 mm beyond the outer edge of perimetrical seal 22.

Panty liner 20 is prepared for use by removing (i.e. peeling) back protector 29; and by then adhering panty liner 20 to the inside surface of the user's panty crotch with adhesive 28. After use, panty liner 20 is peeled from the panty crotch and disposed of hygenically.

Referring now to FIG. 6, it is a fragmentary plan view which shows, on its right end, webs of the laminae from which panty liner 20 is fabricated; and, on its left side, the pattern of the rows 31 of bonds 32, and perimetrical seal 22 which join the laminae together. As stated hereinbefore, the rows 31 of bonds 32 have a length EW that is greater than the desired width of perimetrical edge 21, FIG. 3a. Thus, the bonded laminae, FIG. 6, may be severed simultaneously along a line of parting to free a discrete panty liner 20 from the parent laminae webs; and the line of parting does not have to be precisely registered with perimetrical seal 22 in order to be assured of precipitating the desired scalloping of perimetrical edge 21. Preferably, the laminae webs are continuous so that they can be converted into an endless stream of discrete panty liners upon passing through a bonding station (e.g., preferably ultrasonic) and an adhesive application station.

While a particular embodiment of the present invention has been illustrated and described, it would be obvious to those skilled in the art that various changes and modifications can be made without departing from the spirit and scope of the invention. It is intended to cover in the appended claims all such changes and modifications that are within the scope of this invention.

What is claimed is:

1. A method of making a laminated disposable absorbent product having a scalloped perimetrical edge wherein each scallop is a resilient cushion comprising an edge portion of a resilient lamina of said product, said method comprising:
   juxtaposing webs of the laminae constituents of said product, said webs being greater in area than the finished area of said product whereby said product can be separated from the edge portions of the laminae along a perimetrical line of parting;
   bonding the laminae together with a multiplicity of discrete perimetrically spaced, compacted bonded zones which are disposed to span said line of parting, and which bonded zones are sufficiently thinner than the sum of the thicknesses of uncompacted areas of said laminae to impart a scalloped character to said perimetrical edge; and
   severing said laminae along said line of parting to separate said product from said webs to thereby form said scalloped perimetrical edge.

2. The method of making the laminated disposable absorbent product of claim 1 wherein each said bonded zone is elongate and is oriented with its length generally orthogonal with respect to said line of parting.

3. The method of making the laminated disposable product of claim 2 wherein each elongate said bonded zone comprises a linear array of concatenated discrete bonds.

4. The method of claims 2 or 3 wherein said elongate bonded zones have greater lengths than the desired width of said scalloped perimetrical edge.

* * * * *